(12) United States Patent
Lin et al.

(10) Patent No.: US 11,094,065 B2
(45) Date of Patent: Aug. 17, 2021

(54) METHOD AND SYSTEM FOR AUTOMATICALLY DELINEATING STRIATUM IN NUCLEAR MEDICINE BRAIN IMAGE AND CALCULATING SPECIFIC UPTAKE RATIO OF STRIATUM

(71) Applicant: Chung Yuan Christian University, Taoyuan (TW)

(72) Inventors: Wen-Chen Lin, Taoyuan (TW); Kang-Ping Lin, Taoyuan (TW)

(73) Assignee: Chung Yuan Christian University, Taoyuan (TW)

( * ) Notice: Subject to any disclaimer, the term of this patent is extended or adjusted under 35 U.S.C. 154(b) by 102 days.

(21) Appl. No.: 16/840,441

(22) Filed: Apr. 5, 2020

(65) Prior Publication Data

US 2021/0110544 A1 Apr. 15, 2021

(30) Foreign Application Priority Data

Oct. 9, 2019 (TW) .................................. 108136756

(51) Int. Cl.
*G06K 9/00* (2006.01)
*G06T 7/00* (2017.01)
(Continued)

(52) U.S. Cl.
CPC ............ *G06T 7/0014* (2013.01); *A61B 6/037* (2013.01); *A61B 6/501* (2013.01); *A61B 6/5205* (2013.01);
(Continued)

(58) Field of Classification Search
CPC .................................................. G06T 7/0014
See application file for complete search history.

(56) References Cited

U.S. PATENT DOCUMENTS 10,055,665 B2 8/2018 Akamatsu et al.
2010/0312105 A1* 12/2010 Hurtt .................. A61K 51/0455
600/431
(Continued)

FOREIGN PATENT DOCUMENTS

CN 105392500 3/2016
CN 105816197 8/2016
(Continued)

OTHER PUBLICATIONS

Benjamin M.W. Tsui et al., "Design and Clinical Utility of a Fan Beam Collimator for SPECT Imaging of the Head," The Journal of Nuclear Medicine, vol. 27, No. 6, Jun. 1986, pp. 810-819.
(Continued)

*Primary Examiner* — Oneal R Mistry
(74) *Attorney, Agent, or Firm* — JCIPRNET

(57) ABSTRACT

A method and a system are provided for automatically delineating a striatum in a nuclear medicine brain image and calculating a striatum specific uptake ratio. In the method, initially, a target image is obtained. Then, the target image is projected to a space coordinate to generate a projection amount; an upper end and a lower end of a brain are obtained; and a preset range from the upper to the lower ends is set as a striatum slice area in the target image. A brain area is determined from the target image by a line detection method. Then, a brain volume template is deformed according to the brain area and the striatum slice area, so that a striatum in the brain volume template corresponds to the target image to delineate a striatum region of the target image. Finally, a specific uptake ratio of the striatum region can be calculated.

17 Claims, 10 Drawing Sheets

(51) Int. Cl.
  *G06T 7/12*  (2017.01)
  *A61B 6/03*  (2006.01)
  *A61B 6/00*  (2006.01)

(52) U.S. Cl.
  CPC ...... *G06T 7/12* (2017.01); *G06T 2207/10108* (2013.01); *G06T 2207/30016* (2013.01)

(56) References Cited

U.S. PATENT DOCUMENTS

| | | | |
|---|---|---|---|
| 2016/0183897 A1* | 6/2016 | Rosser | A61B 6/481 600/425 |
| 2016/0260216 A1 | 9/2016 | Wu et al. | |
| 2018/0000440 A1* | 1/2018 | Nishikawa | G01T 1/1642 |

FOREIGN PATENT DOCUMENTS

| | | |
|---|---|---|
| CN | 106687824 | 5/2017 |
| JP | 6360417 | 7/2018 |
| TW | 201641077 | 12/2016 |
| TW | I587841 | 6/2017 |

OTHER PUBLICATIONS

B Jeon et al., "Dopamine transporter imaging with [123I]-β-CIT demonstrates presynaptic nigrostriatal dopaminergic damage in Wilson's disease," J Neurol Neurosurg Psychiatry, Jul. 1998, pp. 60-64.

Naftali Raz et al., "Differential Aging of the Human Striatum: Longitudinal Evidence," AJNR Am J Neuroradiol 24, Oct. 2003, pp. 1849-1856.

Berengere Aubert-Broche et al., "A new improved version of the realistic digital brain phantom," NeuroImage, vol. 3, Issue 1, Aug. 2006, pp. 138-145.

Xu Jing-Feng et al., "MRI scan of striatum volume in healthy adults," Journal of Zhejiang University (Medical Sciences), vol. 39, No. 2, Feb. 2010, pp. 1-8.

Phillip Hsin Kuo et al., "Receiver-Operating-Characteristic Analysis of an Automated Program for Analyzing Striatal Uptake of 123I-Ioflupane SPECT Images: Calibration Using Visual Reads," Journal of Nuclear Medicine Technology, vol. 41, No. 1, Mar. 2013, pp. 26-31.

A. Ninerola et al., "QuantiDOPA: A Quantification Software for Dopaminergic Neurotransmission SPECT," Synthetic Atrial Electrogram Generator, Jan. 2014, pp. 1-4.

Karen Van Audenhaege et al., "Review of SPECT collimator selection, optimization, and fabrication for clinical and preclinical imaging," Med Phys, vol. 42, No. 8, Aug. 2015, pp. 4796-4813.

Amal Elkattan et al., "A Study of Volumetric Variations of Basal Nuclei in the Normal Human Brain by Magnetic Resonance Imaging," Clinical Anatomy, vol. 30, Issue 2, Jan. 2017, pp. 175-182.

Cheng-Han Wu et al., "Effects of 99mTc-TRODAT-1 drug template on image quantitative analysis," PLOS One, Mar. 2018, pp. 1-13.

Ana M. Catafau et al., "Impact of Dopamine Transporter SPECT Using 123I-Ioflupane on Diagnosis and Management of Patients With Clinically Uncertain Parkinsonian Syndromes," Movement Disorders, vol. 19, No. 10, Oct. 2004, pp. 1175-1182.

\* cited by examiner

METHOD AND SYSTEM FOR AUTOMATICALLY DELINEATING STRIATUM IN NUCLEAR MEDICINE BRAIN IMAGE AND CALCULATING SPECIFIC UPTAKE RATIO OF STRIATUM

CROSS-REFERENCE TO RELATED APPLICATION

This application claims the priority benefit of Taiwan application serial no. 108136756, filed on Oct. 9, 2019. The entirety of the above-mentioned patent application is hereby incorporated by reference herein and made a part of this specification.

BACKGROUND OF THE INVENTION

1. Field of the Invention

The invention relates to a nuclear medicine brain image analysis technology, in particular to a method and a system for automatically delineating a striatum in a nuclear medicine brain image and calculating a specific uptake ratio of the striatum.

2. Description of Related Art

A nuclear medicine dopamine image is a tool used to assist in the early diagnosis of primary parkinsonism. A dopamine transporter (DaT) is a special expression protein on dopamine neurons. As the neurons degenerate, the number of these dopamine transporter proteins is also reduced. The dopamine image is an evaluation of the activity of striatal dopamine neurons in the brain by labeling dopamine substances with a nuclear medicine, thereby assisting clinicians in determining whether motor neurological disorders are caused by dopamine neurodegeneration.

Since different types of Parkinsonian syndromes have different therapies and different prognoses, for example, vascular parkinsonism is caused by continuous mild strokes occurring near the basal ganglia controlling motions, and manganese poisoning can also cause symptoms of parkinsonism. The Parkinsonian syndromes have different therapies and different prognoses, so it is clinically important to effectively distinguish between "primary parkinsonism" and other Parkinsonian syndromes.

However, clinically, assistance with a dopamine image, for example, a medical image of single-photon emission computed tomography (SPECT) or positron emission tomography (PET) or other technologies, is needed to accurately classify different types of parkinsonism. By determination of the dopamine image of SPECT imaging, it is traditionally necessary to rely on a professional physician to adjust the image to evaluate whether the striatum function is degraded, and perform semi-quantitative analysis to calculate the specific uptake ratio. In general, the physician will select the range on several tomographic images one by one to calculate the specific uptake ratio by using the counts in the selected range. However, this is time-consuming and laborious and lacks objectivity, and even human errors occur.

SUMMARY OF THE INVENTION

In view of this, the invention provides a method and a system for automatically delineating a striatum in a nuclear medicine brain image and calculating a specific uptake ratio of the striatum, which can automatically select a volume of interest in the nuclear medicine brain image and calculate the specific uptake ratio of the striatum according to the radiopharmaceutical content in the volume of interest.

The invention provides a method for automatically calculating a specific uptake ratio of a striatum. The method includes the following steps. A target image is obtained, where the target image includes a nuclear medicine brain image. The target image is projected to a space coordinate to generate a projection amount. An upper end and a lower end of a brain are obtained in the target image based on a pixel gray value of the projection amount. A preset range from the upper end to the lower end is set as a striatum slice area in the target image. A brain area is determined from the target image by using a line detection method. A brain volume template is deformed according to the brain area and the striatum slice area, a striatum in the brain volume template is mapped to the brain area in the target image, and a striatum region in the target image is delineated. Counts of the striatum region are calculated as first average counts. Another area of the target image is set as a background area, and counts of the background area are calculated as second average counts. A specific uptake ratio of the target image is calculated according to the first average counts and the second average counts.

In an embodiment of the invention, before projecting the target image to the space coordinate to generate the projection amount, the method further includes: image spatial resolution conversion is performed on the target image.

In an embodiment of the invention, obtaining the upper end and the lower end of the brain in the target image based on the pixel gray value of the projection amount includes: searching is performed from an upper end point of the projection amount from top to bottom to a preset position, and a coordinate position of a pixel gray trough value from the upper end point to the preset position is taken as the upper end. Searching is performed from a lower end point of the projection amount from bottom to top to the preset position, and a coordinate position of a pixel gray trough value from the lower end point to the preset position is taken as the lower end.

In an embodiment of the invention, the preset position is ½ of an axial height of the projection amount.

In an embodiment of the invention, the preset range is ½ to ⅔ of an axial height difference of the projection amount from the upper end to the lower end.

In an embodiment of the invention, determining the brain area from the target image by using the line detection method includes: a plurality of target image slices of the target image in a range from the upper end to the lower end are extracted one by one. An image center of the target image slices is set as a picture center of a polar coordinate, and the target image slices are transformed from Cartesian coordinates to polar coordinates. An image boundary is detected to define a brain contour in the transformed target image slices. The target image slices having the brain contour are transformed back to the Cartesian coordinates, and the brain area is determined from the target image.

In an embodiment of the invention, deforming the brain volume template according to the brain area and the striatum slice area, mapping the striatum in the brain volume template to the brain area in the target image, and delineating the striatum region in the target image include: vertical axis scaling is performed on the brain volume template according to the upper end, the lower end, and the striatum slice area. Horizontal axis distortion is performed on the scaled brain volume template by using a thin plate spline method. The striatum in the adjusted brain volume template is mapped to the brain area in the target image. The striatum region in the target image and a center position of the striatum region are delineated.

In an embodiment of the invention, calculating the counts of the striatum region as the first average counts includes: the first average counts of the striatum region to be calculated according to total counts and total area of the striatum region.

In an embodiment of the invention, the background area includes an occipital lobe area, and calculating counts of the area as the second average counts includes: a slice range to be set downward from a position of the slice where the striatum slice area first appears from the upper end point of the projection amount from top to bottom. The occipital lobe area is delineated in the slice range according to a divided area. The second average counts of the occipital lobe area are calculated according to total counts and total area of the occipital lobe area.

In an embodiment of the invention, the background area includes a cerebellum area, and calculating counts of the cerebellum area as the second average counts includes: a slice range to be set downward according to a position of the lower end of the brain. The cerebellum area is delineated in the slice range according to a divided area. The second average counts of the cerebellum area are calculated according to total counts and total area of the cerebellum area.

In an embodiment of the invention, the background area includes a whole brain area, and calculating counts of the whole brain area as the second average counts includes: the second average counts to be calculated according to total counts and total area of a portion of the brain area minus the striatum region.

In an embodiment of the invention, calculating the specific uptake ratio of the target image according to the first average counts and the second average counts includes: the second average counts to be subtracted from the first average counts and the difference to be divided by the second average counts to obtain the specific uptake ratio.

The invention further provides a method for automatically delineating a striatum in a nuclear medicine brain image. The method includes the following steps: to obtain a target image, containing a nuclear medicine brain image. The target image is projected to a space coordinate to generate a projection amount. An upper end and a lower end of a brain are obtained in the target image based on a pixel gray value of the projection amount. A preset range from the upper end to the lower end is set as a striatum slice area in the target image. A brain area is determined from the target image by using a line detection method. A brain volume template is deformed according to the brain area and the striatum slice area, and a striatum in the brain volume template is mapped to the brain area in the target image. A striatum region in the target image is delineated.

The invention further provides a system for automatically calculating a specific uptake ratio of a striatum. The system includes an image receiver and an electronic device. The image receiver is configured to receive a target image. The target image includes a nuclear medicine brain image. The electronic device includes a storage device and a processor. The storage device stores one or more instructions. The processor is configured to execute the instruction to obtain the target image; project the target image to a space coordinate to generate a projection amount; obtain an upper end and a lower end of a brain in the target image based on a pixel gray value of the projection amount; set ½ to ⅔ of an axial height difference of the projection amount from the upper end to the lower end as a striatum slice area in the target image; determine a brain area from the target image by using a line detection method; deform a brain volume template according to the brain area and the striatum slice area, map a striatum in the brain volume template to the brain area in the target image, and delineate a striatum region in the target image; calculate counts of the striatum region as first average counts; set another area of the target image as a background area, and calculate counts of the background area as second average counts; and calculate a specific uptake ratio of the target image according to the first average counts and the second average counts.

To make the features and advantages of the invention clear and easy to understand, the following gives a detailed description of embodiments with reference to accompanying drawings.

DESCRIPTION OF THE EMBODIMENTS

According to the invention, a brain area and a striatum slice area are determined in a nuclear medicine brain image according to coordinate positions. Scaling and distortion are performed on a brain volume template according to the determined brain area and striatum slice area to delineate a striatum region in the nuclear medicine brain image. After obtaining a range of each volume of interest in the nuclear medicine brain image, a specific uptake ratio of a striatum based on different background areas is calculated by calculating average counts of each area. Thereby, the time for manually selecting the volume of interest can be reduced, and human errors can be avoided.

Figure 1:
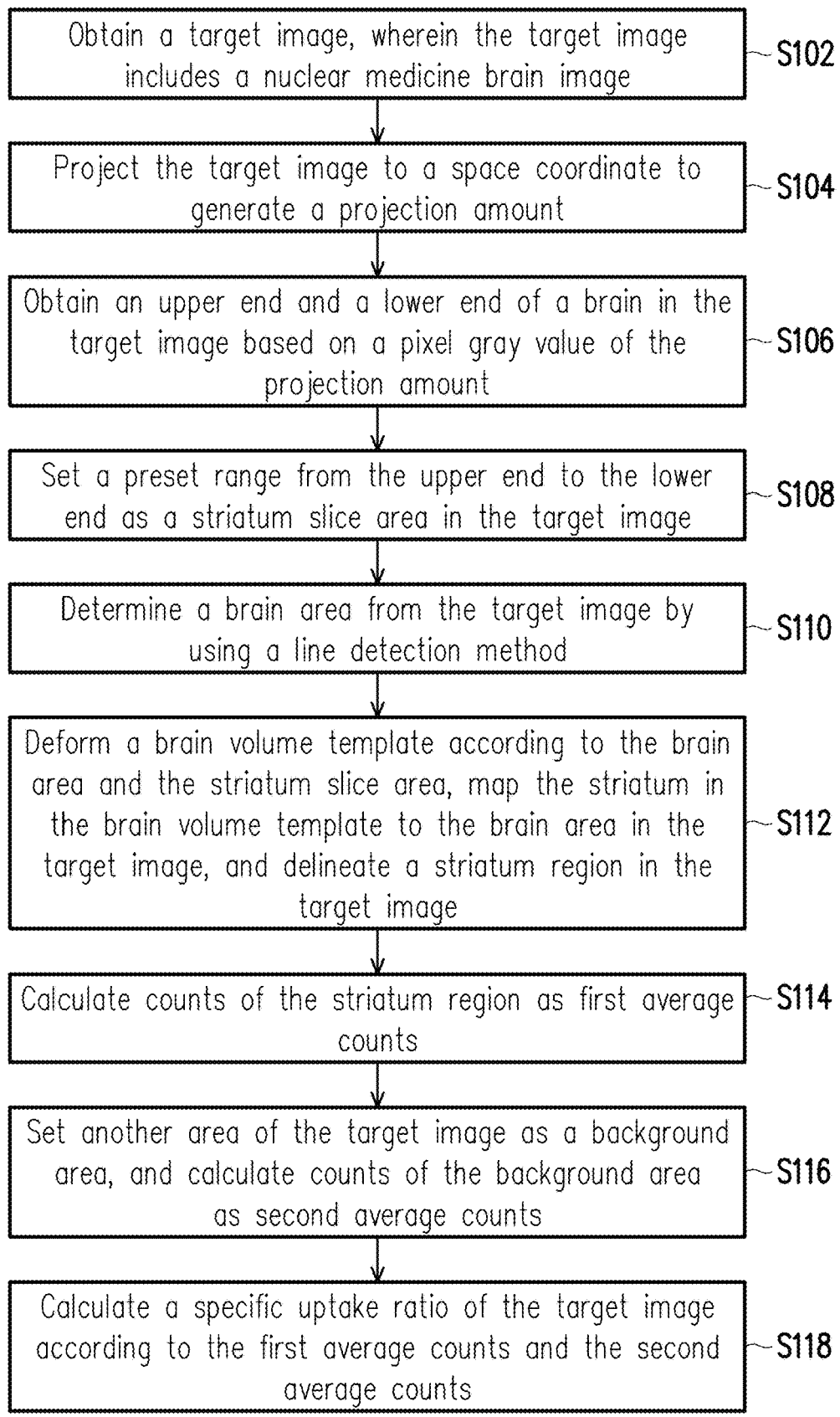
FIG. 1 shows a flow chart of a method for automatically calculating a specific uptake ratio of a striatum according to an embodiment of the invention.
Figure 10:
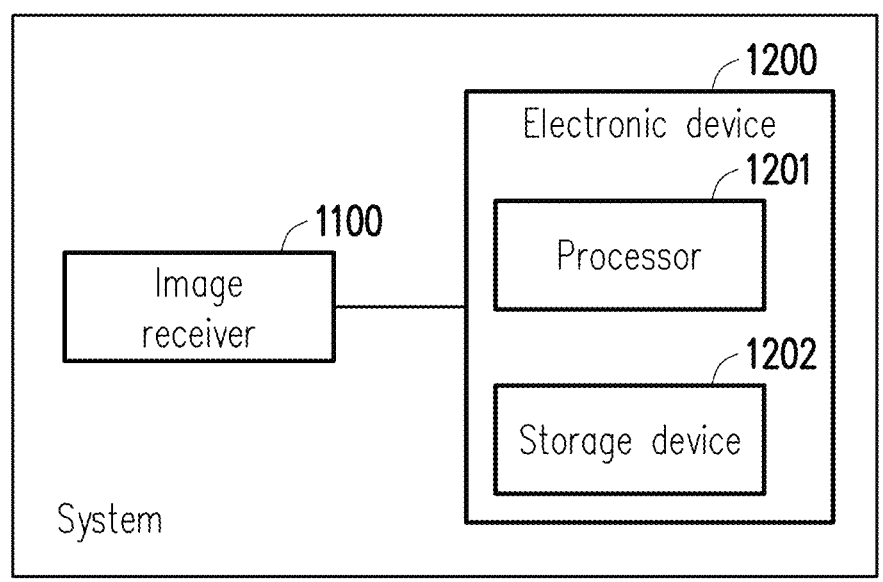
FIG. 10 shows a block diagram of a system for automatically calculating a specific uptake ratio of a striatum according to an embodiment of the invention.

FIG. 1 shows a flow chart of a method for automatically calculating a specific uptake ratio of a striatum according to an embodiment of the invention. FIG. 10 shows a block diagram of a system for automatically calculating a specific uptake ratio of a striatum according to an embodiment of the invention. Referring to FIG. 10, a system 1000 for automatically calculating a specific uptake ratio of a striatum includes an image receiver 1100 and an electronic device 1200. The image receiver 1100 is coupled to the electronic device 1200 and may be connected to the electronic device 1200 in a wired or wireless manner to transmit data.

The image receiver 1100 receives a target image generated by an image capturing device. The image capturing device performs 180-degree or 360-degree rotary scanning around a patient by using a scanning instrument, and collects a radiation signal emitted by a radiopharmaceutical ingested by the patient at the scanned site. Next, the collected radiation signal is properly converted to generate a three-dimensional image. The image obtained by the scanning may include a sagittal plane, a coronal plane or a transverse plane, or even a tomographic image at any angle. The scanning instrument is, for example, a medical instrument such as a single-photon emission computed tomography (SPECT) instrument, but the invention is not limited thereto.

The term target image herein refers to a nuclear medicine brain image obtained by scanning a target organ with a scanning instrument and performing reformation. The target image includes a plane image reconstructed from a three-dimensional volume image, including a sagittal plane slice image, a coronal plane slice image, and a transverse plane slice image. In addition, a volume of interest of the brain in a nuclear medicine brain image generally includes at least a cerebral part region, a striatum region, an occipital lobe region, and a cerebellum region.

The electronic device 1200 includes a processor 1201 and a storage device 1202. The electronic device 1200 may be a device with an arithmetic function such as a personal computer, a notebook computer and a remote host, but the invention is not limited thereto.

In various embodiments, the processor 1201 is, for example, a central processing unit (CPU) or a graphics processing unit (GPU), or another programmable general purpose or special purpose microprocessor, a digital signal processor (DSP), a programmable controller, an application specific integrated circuit (ASIC), a programmable logic device (PLD), or another similar device or a combination of the above devices. The processor 1201 is coupled to the storage device 1202, and is accessible and is configured to execute an instruction recorded in the storage device 1202 to implement a method for automatically calculating a specific uptake ratio of a striatum according to embodiments of the invention.

The storage device 1202 is, for example, any type of fixed or movable random access memory (RAM), read-only memory (ROM), flash memory, or another similar device or a combination of the above devices, and is configured to record one or more instructions executable by the processor 1201. The instructions can be loaded into the processor 1201.

Referring to FIG. 1 and FIG. 10 simultaneously, the method of the present embodiment is applicable to the above-mentioned system 1000, and detailed steps of the method for automatically calculating the specific uptake ratio of the striatum of the present embodiment will be described below in conjunction with the various devices and elements of the system 1000.

First, the processor 1201 obtains a plurality of reformed and converted target images received by the image receiver 1100, where the target image includes a nuclear medicine brain image (step S102). After obtaining the target image, the processor 1201 calculates parameters of spatial resolution of the obtained target image (for example, x=A(mm); y=B(mm); z=C(mm)). In order to meet the resolution required by the method designed in the present embodiment, after obtaining the target image, the processor 1201 first performs image spatial resolution conversion on the target image. Specifically, the processor 1201 may convert the spatial resolution parameters of the target image to x=D (mm); y=E(mm); z=F(mm) by using an interpolation method.

For example, in the present embodiment, the target image is a nuclear medicine brain image. Assuming that the spatial resolution of the original target image captured by the image receiver 1100 is x=3.895 (mm); y=3.895 (mm); z=3.895 (mm), after re-slicing the original target image by the interpolation method, the resolution can be converted to x=1.000 (mm); y=1.000 (mm); z=1.000 (mm). The interpolation method is, for example, nearest neighbor interpolation, bilinear interpolation or bicubic interpolation, but the invention is not limited thereto.

Next, the processor 1201 determines a brain area and a striatum slice area in the target image. First, the processor 1201 projects the target image to a spatial coordinate to generate a projection amount (step S104). Next, the processor 1201 obtains an upper end and a lower end of a brain in the target image based on a pixel gray value of the projection amount (step S106). In detail, the processor 1201 projects the target image to the spatial coordinate to generate the projection amount of the target image, and obtains the upper end and the lower end of the brain in the target image based on the projection amount by using the pixel gray value. In an embodiment, the processor 1201 searches from an upper end point of the projection amount from top to bottom to a preset position, and then takes a coordinate position of a pixel gray trough value from the upper end point to the preset position as the upper end. Besides, the processor 1201 searches from a lower end point of the projection amount from bottom to top to the preset position, and then takes a coordinate position of a pixel gray trough value from the lower end point to the preset position as the lower end. The invention does not limit the preset position for setting the search range here, which may be, for example, a position of ½ of an axial height of the projection amount. Then, the processor 1201 sets the preset range from the upper end to the lower end as the striatum slice area in the target image (step S108). In an embodiment, the processor 1201 sets the slice included in the preset coordinate range of the projection amount in the range from the upper end to the lower end as the striatum slice area. The invention does not limit the preset coordinate range here, which may be, for example, a range of ½ to ⅔ of the axial height difference of the projection amount from the upper end to the lower end. Finally, the processor 1201 determines the brain area from the target image by using a line detection method.

Figure 2:
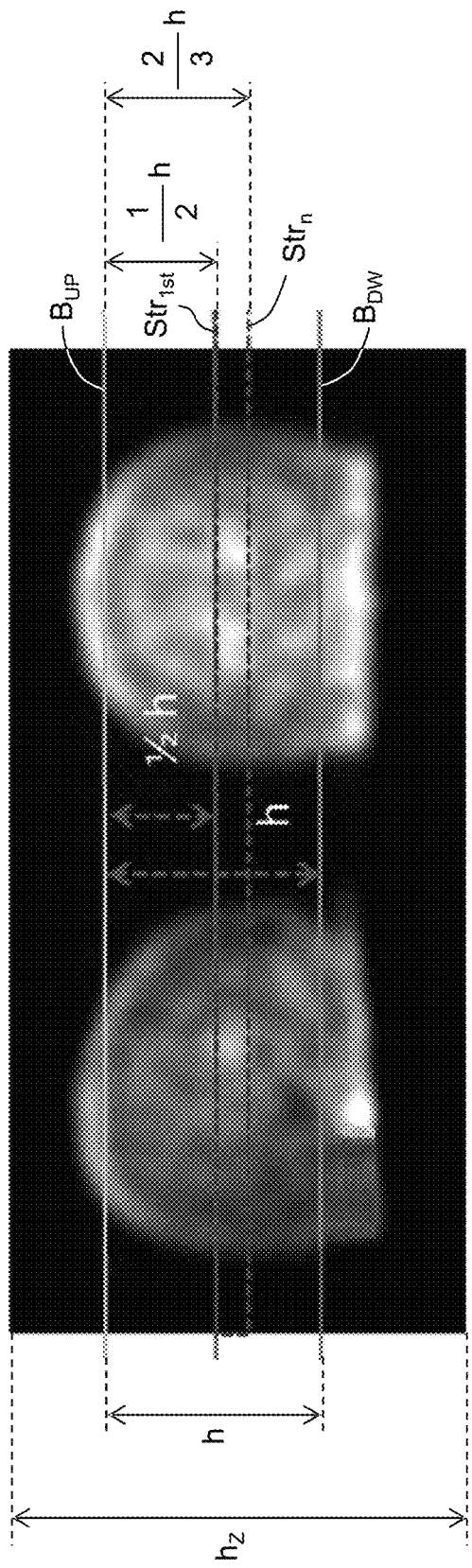
FIG. 2 shows an example of a totaled target image according to an embodiment of the invention.

The details of steps S104 to S108 will be described below with reference to an embodiment. In the present embodiment, the top and bottom boundaries of the brain area in the target image must first be determined to determine the top and bottom ranges of the brain area. FIG. 2 shows an embodiment of the invention. Referring to FIG. 2, the processor 1201 performs a totaling calculation of sagittal plane and coronal plane slices of the target image to generate a projection amount, and obtains a totaled sagittal plane slice image as shown on the left side of FIG. 2; and a totaled coronal plane slice image on the right side. Next, the processor 1201 performs a projection calculation on the z-axis of the totaled target image, and defines a total z-axis height $h_z$. Next, the processor 1201 searches the totaled sagittal plane and coronal plane slice images from the upper end point of the z-axis projection amount from top to bottom to ½ of the total z-axis height $h_z$, and finds the coordinate of the trough value of the pixel gray value and defines the coordinate as the "upper end $B_{UP}$" of the top of the brain. In addition, the processor 1201 searches the totaled sagittal plane and coronal plane slice images from the lower end point of the z-axis projection amount from bottom to top to ½ of the total z-axis height $h_z$, and finds the coordinate of the trough value of the pixel gray value and defines the coordinate as the "lower end $B_{DW}$" of the bottom of the brain. Besides, the processor 1201 defines the height between the obtained upper end $B_{UP}$ and lower end $B_{DW}$ as a height h. Finally, the slice image area included in the range from a height h/2 to a height 2h/3 between the upper end $B_{UP}$ and the lower end $B_{DW}$ is defined as the striatum slice area, which represents a possible position of the striatum. In other words, the position at the height h/2 between the upper end $B_{UP}$ and the lower end $B_{DW}$ in the target image may be regarded as the first transverse plane striatum slice position $Str_{1st}$ of the striatum slice area, and the position at the height 2h/3 may be regarded as the last transverse plane striatum slice position $Str_n$ of the striatum slice area.

Figure 3:
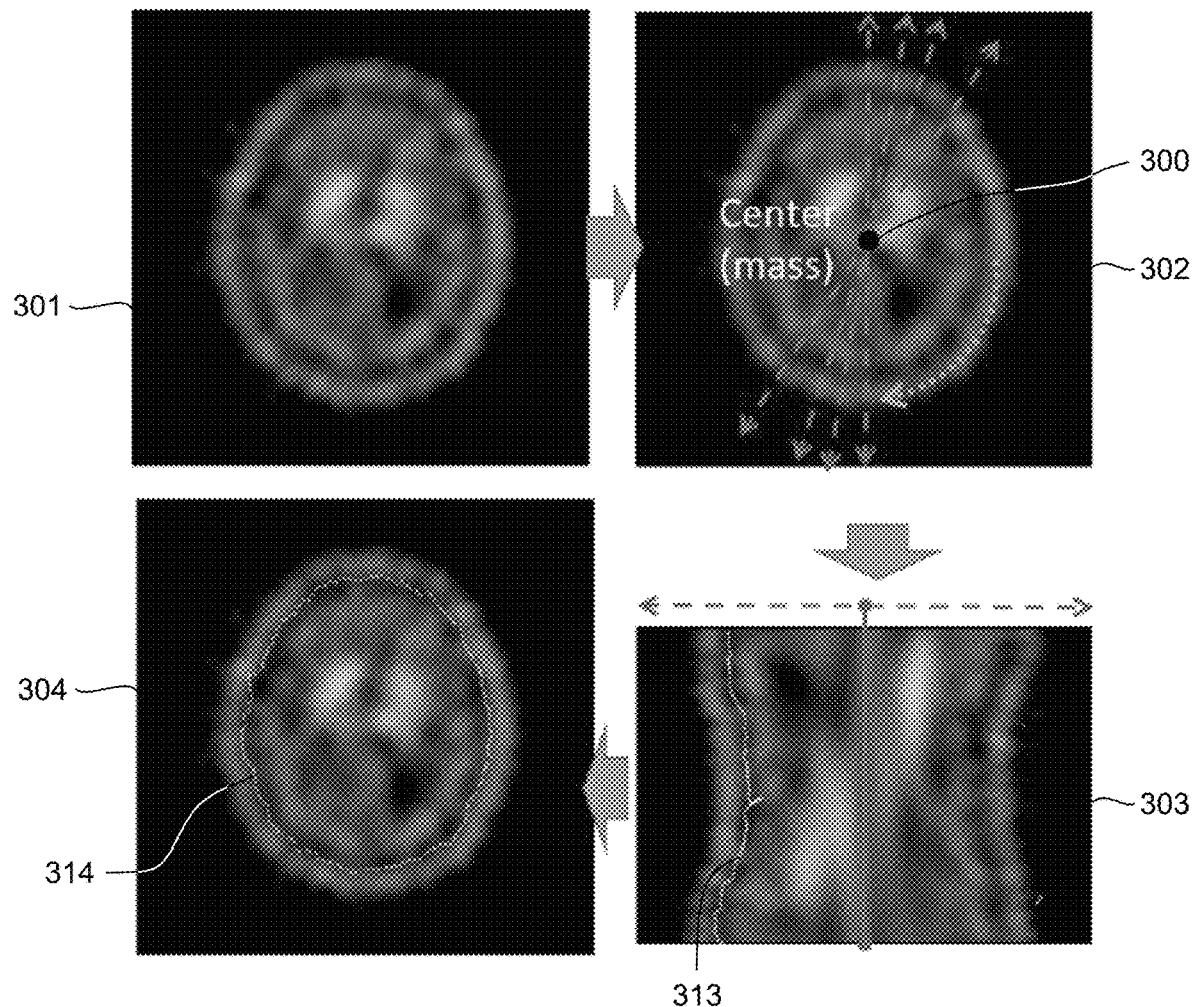
FIG. 3 shows an example of extracting a brain area contour boundary according to an embodiment of the invention.

Next, brain contour detection is performed. The processor 1201 determines a brain area from the target image by using a line detection method (step S110). In the present embodiment, after determining the position parameters of the upper end $B_{UP}$ and the lower end $B_{DW}$ of the brain area, the processor 1201 extracts a plurality of target image slices of the target image in the range from the upper end to the lower end one by one, and sets an image center $(x_0, y_0)$ of each target image slice as a picture center of a polar coordinate. Next, the processor 1201 transforms each of the target image slices from Cartesian coordinates $(x, y)$ to polar coordinates $(r, \theta)$, and detects an image boundary to define a brain contour in each of the transformed target image slices. Next, the processor 1201 transforms the target image slices having the brain contour back to the Cartesian coordinates, and determines the brain area from the target image. Finally, the processor 1201 smoothes all the contours by using an average filter to delineate the brain area from the target image. For example, FIG. 3 shows an example of extracting a brain area contour boundary according to an embodiment of the invention. Referring to FIG. 3, taking the transverse plane slice images 301 to 304 as an example, for the transverse plane slice image 301 of the target image, the processor 1201 transforms the image 302 presented in the Cartesian coordinates $(x, y)$ into the image 303 presented in the polar coordinates $(r, \theta)$ with the center of the image 302 as a picture center 300 of the polar coordinate. For example, the processor 1201 may transform the image 302 presented in the Cartesian coordinates clockwise into the image 303 presented in the polar coordinates every 3° angle with the picture center 300 as the center point, but the invention does not limit the angle for transformation. Next, the processor 1201 obtains an image boundary 313 in the image 303 by using the line detection method, and then transforms the image 303 from the polar coordinates back to the Cartesian coordinates, for example, the image 304, and the boundary 313 is accordingly transformed into a brain area transverse plane contour 314 of the image 304.

Figure 4:
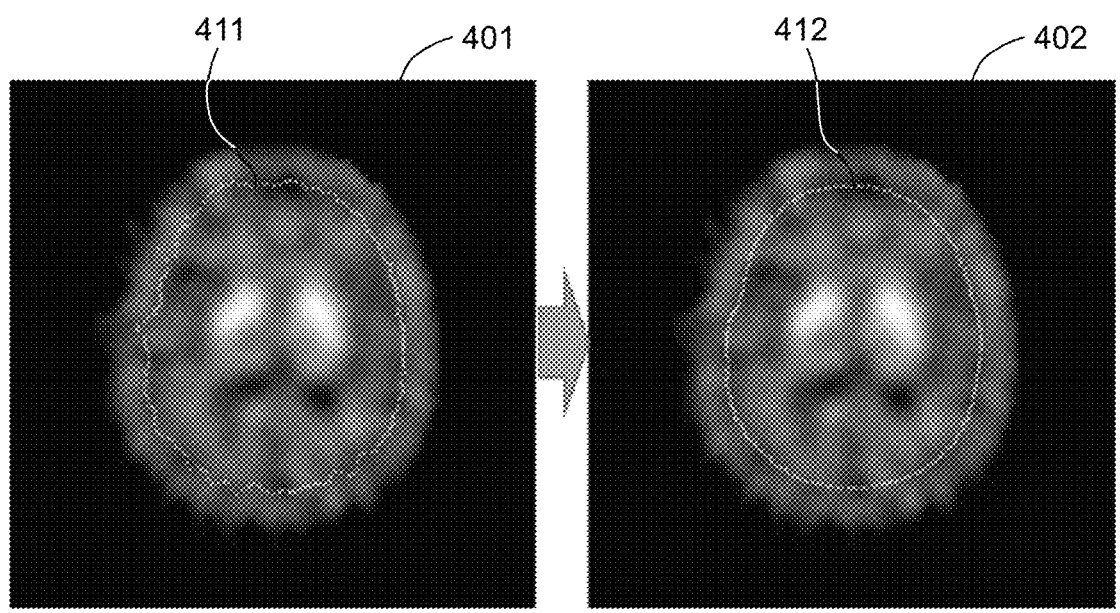
FIG. 4 shows an example of an average filter smoothing a contour according to an embodiment of the invention.

In addition, FIG. 4 shows an example of an average filter smoothing a contour according to an embodiment of the invention. Referring to FIG. 4, the brain area transverse plane contour 411 extracted by the previous step in an image 401 is smoothed by the filter to generate a brain area transverse plane contour 412 in an image 402. The filter may be an average filter or other types of filters, but the invention is not limited thereto.

After the foregoing steps S104 to S110 of determining the positions of the upper end $B_{UP}$ and the lower end $B_{DW}$ of the brain area in the target image by using the pixel gray value, and the step of delineating the brain area contour in each of the transverse plane slice images one by one within the range of the positions of the upper end $B_{UP}$ and the lower end $B_{DW}$ of the brain area, a volume range representing the whole brain area can be selected in the target image in the present embodiment.

Next, the processor 1201 deforms a brain volume template according to the brain area and the striatum slice area, maps the striatum in the brain volume template to the brain area in the target image, and delineates a striatum region in the target image (step S112). In detail, the processor 1201 performs vertical axis scaling on the brain volume template according to the upper end and the lower end of the brain area and the striatum slice area, and performs horizontal axis distortion on the scaled brain volume template by a thin plate spline method. Next, the processor 1201 maps the striatum in the adjusted brain volume template to the brain area in the target image to delineate a striatum region and a center position of the striatum region so as to delineate a striatum region in the target image and a center position of the striatum region.

Figure 5:
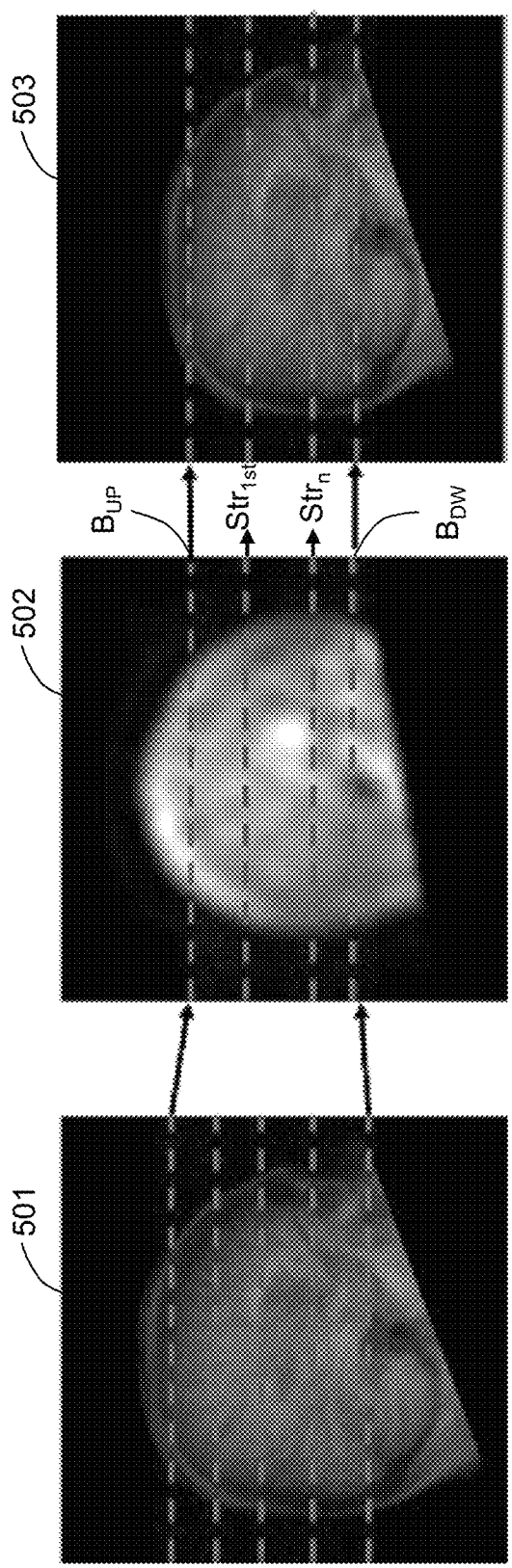
FIG. 5 shows an example of vertical axis scaling of a brain volume template according to an embodiment of the invention.
Figure 6:
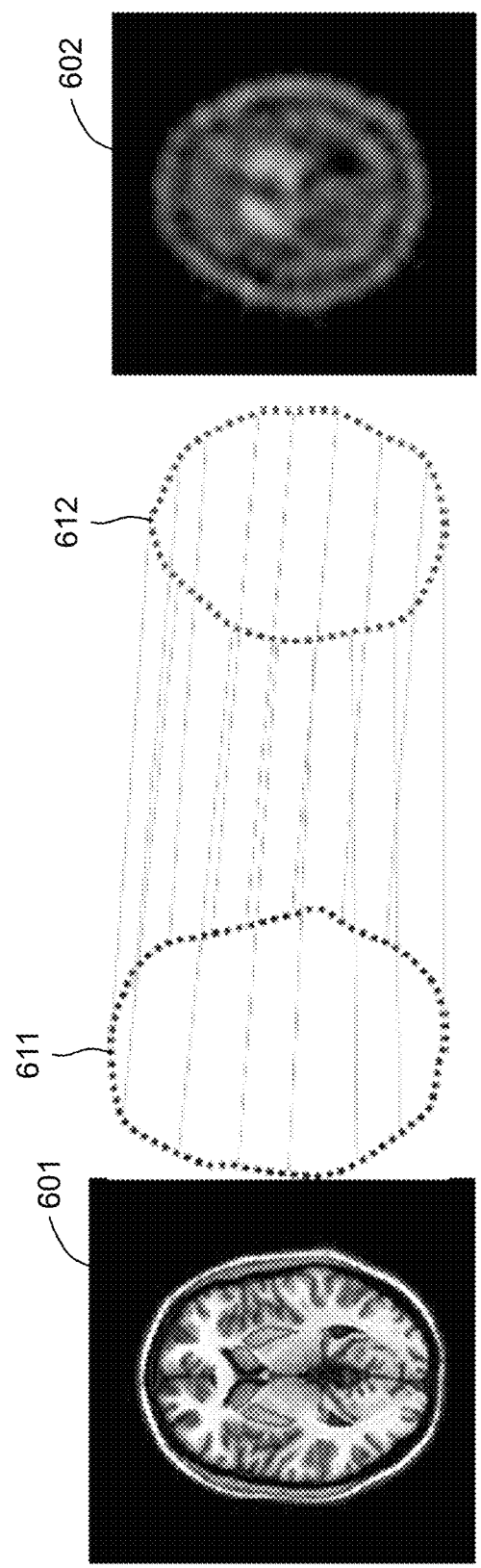
FIG. 6 shows an example of horizontal axis distortion of the brain volume template according to an embodiment of the invention.
Figure 7:
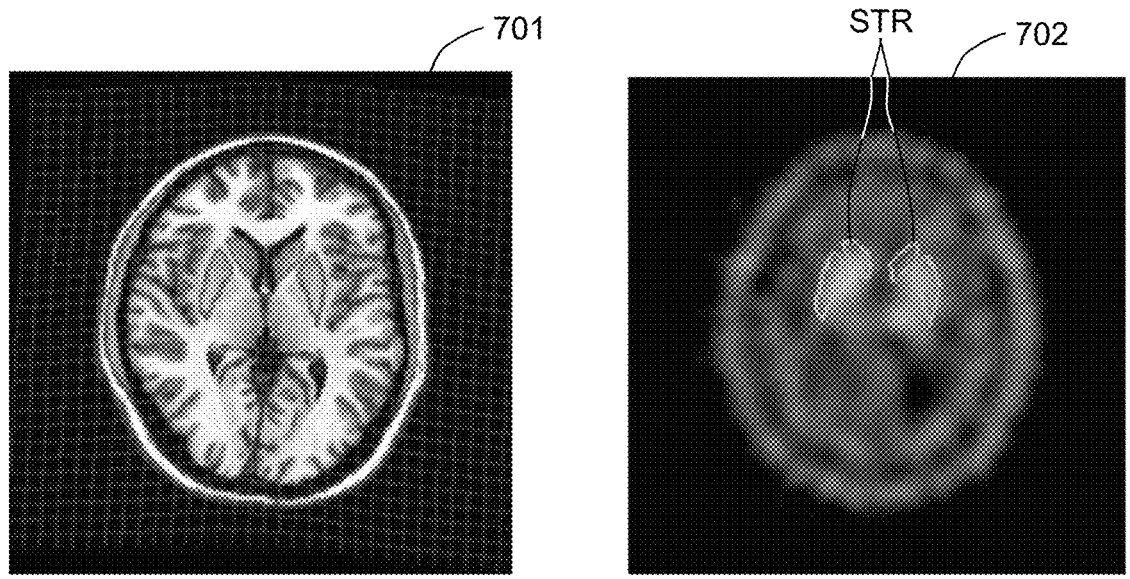
FIG. 7 shows an example of delineating a striatum region according to an embodiment of the invention.

It should be noted that the brain volume template herein is a volume of interest template that is set by using a brain anatomy atlas (for example, a brain anatomy atlas obtained by MRI scanning). The volume of interest template includes at least a volume of interest (a cerebral part region, a striatum region, an occipital lobe region or a cerebellum region) in the brain. The brain volume template may be used for spatial standardization of the whole brain. In the embodiment of FIG. 5 to FIG. 7, a method of scaling and distorting a brain volume template is described by taking a slice image of the brain volume template as an example. However, the method may be applied to all slice images to obtain a complete volume of interest in the target image.

Specifically, FIG. 5 shows an example of vertical axis scaling of a brain volume template according to an embodiment of the invention. Referring to FIG. 5, an image 501 is a schematic view of the brain volume template, and an image 502 is a schematic view of a sagittal plane slice image of the target image. The processor 1201 performs scaling on the vertical axis of the brain volume template according to the positions of the first transverse plane striatum slice position $Str_{1st}$ and the last transverse plane striatum slice position $Str_n$ of the upper end $B_{UP}$ and the lower end $B_{DW}$ of the brain area and the striatum slice area in the image 502, so that the brain volume template is subjected to re-slicing through interpolated values to generate a scaled brain volume template as in an image 503.

Figure 8:
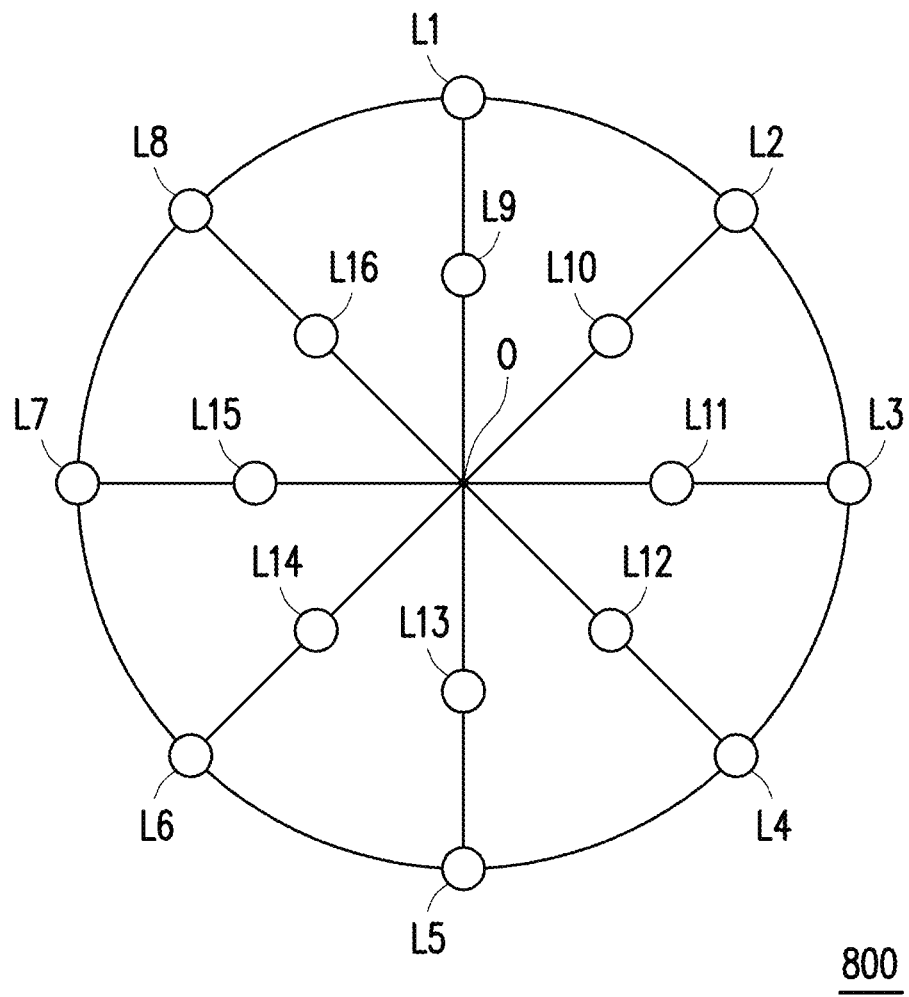
FIG. 8 shows an example of landmarks of a thin plate spline method according to an embodiment of the invention.

In another aspect, the processor 1201 performs distortion on the slice of the horizontal axis slice of the brain volume template in the range from the first transverse plane striatum slice position $Str_{1st}$ to the last transverse plane striatum slice position $Str_n$ in the striatum slice area of the sagittal plane slice image of the target image to which the scaled brain volume template corresponds, to estimate the striatum region and the center position of the striatum region. FIG. 6 shows an implementation example of horizontal axis distortion of the brain volume template according to the invention. Referring to FIG. 6, an image 601 is a slice of a transverse plane image of the brain volume template, and an image 602 is a transverse plane slice of the target image. The processor 1201, for example, matches a brain area transverse plane contour 611 of the image 601 with a brain area contour 612 of the image 602 by using a thin plate spline method to perform image distortion. For example, the thin plate spline method in the slice of each target image requires, for example, 16 landmarks, including 8 landmarks on the smooth contour of the brain and 8 landmarks extending toward a spatial collection point. However, the invention does not limit the number of the landmarks here, and the number of the landmarks may be bigger or smaller. As shown in FIG. 8, FIG. 8 shows an example of landmarks of a thin plate spline method according to an embodiment of the invention. A brain transverse plane contour 800 in FIG. 8 is a schematic view of a smooth brain contour. The landmarks L1 to L8 are intersections between the radial lines every 45° angle from the center position O of the brain area and the smooth contour of the brain area, and the landmarks L9 to L16 are distance points from the center position O to the ½ position of the landmarks L1 to L8. In the present embodiment, the processor 1201 uses the above landmarks L1 to L16 to match the images by the thin plate spline method according to the brain area transverse plane contour 611 and the two brain area transverse plane contours 611 and 612, so that the transverse plane brain image 601 is distorted to conform to the size of the transverse plane brain image 602.

After performing the vertical axis scaling and the horizontal axis distortion on the brain volume template, the contour of the brain volume template can be deformed to conform to the contour of the brain area of the target image. Next, the processor 1201 maps the striatum in the deformed brain volume template to the brain area of the target image to estimate a striatum region and a center position of the striatum region. FIG. 7 shows an example of delineating the striatum region according to an embodiment of the invention. Referring to FIG. 7, an image 701 is a deformed brain volume template, and an image 702 is a slice of the transverse plane slice image of the target image. After the image 701 is mapped to the image 702, a striatum region STR can be delineated from the image 702.

In another embodiment, the processor 1201 checks whether the portion of the $13^{th}$ slice from the uppermost slice image position of the striatum region STR from top to bottom in the range of the delineated striatum region is the largest area of the specific uptake ratio. If not, the range of the striatum region STR is moved 3 slices upward or downward respectively to determine that the $13^{th}$ slice of the striatum region STR is in the slice area having the largest specific uptake ratio.

The method for automatically delineating the striatum in the nuclear medicine brain image provided by the invention includes the above steps S102 to S112. By performing the vertical axis scaling and the horizontal axis distortion on the brain volume template and mapping the striatum in the deformed brain volume template to the brain area of the target image, a volume range representing the whole striatum region can be selected in each of the transverse plane slice images in the range from the first transverse plane striatum slice position $Str_{1st}$ to the last transverse plane striatum slice position $Str_n$ of the striatum slice area in the target image one by one.

In the system and the method for automatically calculating the specific uptake ratio of the striatum provided in the invention, the processor 1201 is configured to calculate the specific uptake ratio of the striatum in addition to the above steps S102 to S112. The processor 1201 calculates counts of the striatum region as first average counts (step S114). Besides, the processor 1201 sets another area of the target image as a background area, and calculates counts of the background area as second average counts (step S116). The another area commonly used as the background region in the target image includes a whole brain area, an occipital lobe area, and a cerebellum area. The background area may also be another part of the brain area, but the invention is not limited thereto. Specifically, the processor 1201 calculates the total counts in the striatum region divided by the total area as the first average counts. The total counts are an important indicator for the evaluation of the drug absorption amount of the organ by the nuclear medicine examination. The average counts of the radiopharmaceutical (marker) are calculated by dividing the total counts of the marker in the volume of interest by the total area in the volume of interest. It can be expressed as equation (1):

$$\text{Average counts} = \frac{\text{total counts of marker in stereo region of interest}}{\text{total area in stereo region of interest}} \quad (1)$$

Since the striatum region is divided into the left and right sides, a portion of calculating average counts of the striatum region by using equation (1) may be expressed as equation (2), that is, the processor 1201 calculates the average counts of the striatum region by dividing the total counts in the striatum regions on the left and right sides by the total area in the striatum regions on the left and right sides.

$$\text{Average counts of striatum region} = \frac{\text{total counts of left striatum region} + \text{total counts of right striatum region}}{\text{total area of left striatum region} + \text{total area of right striatum region}} \quad (2)$$

A portion of calculating average counts of the striatum region on a single side by using equation (1) may be expressed as equation (3):

$$\text{Average counts of single-side striatum region} = \frac{\text{total counts of single-side striatum region}}{\text{total area of single-side striatum region}} \quad (3)$$

In a portion of calculating average counts of the whole brain area, since the whole brain area is mainly used as a background area for semi-quantitative analysis, it is necessary to subtract the range of the striatum regions on the left and right sides from the brain area to obtain the whole brain area. In detail, the processor 1201 calculates the average counts of the whole brain area according to the total counts and the total area of the portion of the brain area minus the striatum region. That is, the processor 1201 obtains the average counts of the whole brain area according to the following equation (4).

$$\text{Average counts of whole brain area} = \frac{\text{total counts of whole brain area} - \text{total counts of striatum region}}{\text{total area of whole brain area} - \text{total area of striatum region}} \quad (4)$$

Figure 9:
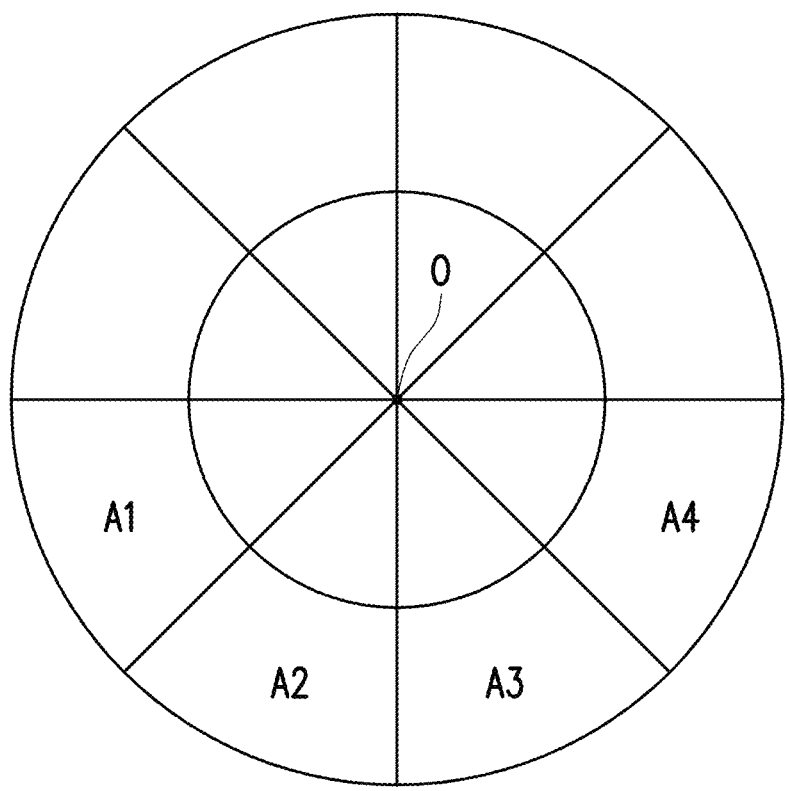
FIG. 9 shows an example of brain area division according to an embodiment of the invention.

In a portion of calculating average counts of the occipital lobe area, the range of the occipital lobe area must first be determined. In the present embodiment, the processor 1201 estimates the occipital lobe area according to a position of the striatum region in the target image. Specifically, the processor 1201 estimates a slice range of the occipital lobe area according to a position of the slice where the striatum region first appears from the upper end point to the lower end point of the projection amount. Next, the processor 1201 delineates the occipital lobe area in the estimated slice range according to the set divided area. FIG. 9 shows an example of brain area division according to an embodiment of the invention. Referring to FIG. 9, a brain transverse plane contour 900 is a schematic view of a smooth brain contour. Divided areas A1 to A4 are divided according to intersections between the radial lines every 45° angle from the center position O of the brain area and the smooth contour of the brain area, and distance points from the center position O to the ½ position of each of the intersections. The processor 1201 uses the $10^{th}$ slice from the transverse plane striatum slice position $Str_{1st}$ where the delineated striatum region first appears from top to bottom from the z-axis position of the target image as an initial slice So of the occipital lobe area (i.e., $So=Str_{1st}+10$). In a range 10 slices downward from the initial slice So, an area corresponding to the divided areas A1 to A4 is delineated from the So to So+10 slices as the occipital lobe area according to a division manner in the brain transverse plane contour 900, which represents the volume range of the whole occipital lobe area.

However, the invention does not limit the number of slices in the slice range here. The processor 1201 calculates average counts of the occipital lobe area according to total counts and total area of the occipital lobe area, as in equation (5).

$$\text{Average counts of occipital lobe area} = \frac{\text{total counts of occipital lobe area}}{\text{total area of occipital lobe area}} \quad (5)$$

In a portion of calculating average counts of the cerebellum area, the range of the cerebellum area must first be determined. In the present embodiment, the processor 1201 estimates a slice range of the cerebellum area according to a position of the lower end of the brain area in the projection amount, and delineates the cerebellum area in the slice range according to the set divided area. In detail, the processor 1201 uses the position of the lower end Bow of the brain area obtained in the foregoing step as an initial slice Sc of the cerebellum area. In a range 10 slices downward from the z-axis position of the initial slice Sc, a corresponding area is delineated from the Sc to Sc+10 slices as the cerebellum area according to a division manner of divided areas A2 to A3 in the brain transverse plane contour 900 in FIG. 9 to select the volume range representing the whole cerebellum area. However, the invention does not limit the number of slices in the slice range here. Next, the processor 1201 calculates average counts of the cerebellum area according to total counts and total area of the cerebellum area, as in Equation (6):

$$\text{Average counts of cerebellum area} = \frac{\text{total counts of cerebellum area}}{\text{total area of cerebellum area}} \quad (6)$$

The average counts of the whole brain area, the occipital lobe area and the cerebellum area described above may be used as a background value for calculating the specific uptake ratio of the estimated target image (i.e., the second average counts in the present embodiment). Therefore, as shown in FIG. 10 and FIG. 1, the processor 1201 calculates the specific uptake ratio of the target image according to the first average counts and the second average counts (step S118). The specific uptake ratio is often used in semi-quantitative analysis of a nuclear medicine brain image. The specific uptake ratio is calculated by dividing the difference between the average counts of the target area and the average counts of the background area by the average counts of the background area. A higher specific uptake ratio calculated within a certain target area range represents a higher marker uptake activity of the target area relative to the background area. In the present embodiment, the specific uptake ratio is calculated as follows: the processor 1201 subtracts the average counts of the background area (i.e., brain area, occipital lobe area or cerebellum area) from the average counts of the target area (i.e., striatum region) and divides the difference by the average counts of the background area to obtain the specific uptake ratio. The calculation manner of the specific uptake ratio may be expressed as equation (7):

$$\text{Specific uptake ratio} = \frac{\text{average counts of target area} - \text{average counts of background area}}{\text{average counts of background area}} \quad (7)$$

That is, the processor 1201 can respectively calculate different specific uptake ratios according to the average counts of the striatum region and different background areas such as the brain area, the occipital lobe area, and the cerebellum area, which are provided to medical professional personnel for use according to their experiences and habits.

The invention further provides a non-transitory computer readable recording medium in which a computer program is recorded. The computer program is used to perform the various steps of the above method for automatically calculating the specific uptake ratio of the striatum. The computer program is composed of a plurality of program code segments (for example, an organization chart establishing program code segment, a setting program code segment, and a deploying program code segment), and after the program code segments are loaded in an electronic device and executed, the steps of the above method for automatically calculating the specific uptake ratio of the striatum can be completed.

Based on the above, according to the method for automatically delineating the striatum in the nuclear medicine brain image, the brain area and the striatum slice area are first determined in the nuclear medicine brain image according to the coordinate positions, and then scaling and the distortion are performed on the brain volume template according to the determined brain area and striatum slice area to delineate the striatum region in the nuclear medicine brain image. The ranges of the occipital lobe area and the cerebellum area are estimated according to the positions of the brain area and the striatum region. Thereby, the volume range of each of the volumes of interest can be delineated more accurately while automatically selecting the volume of interest, so that the time for manually selecting the volumes of interest is reduced, and human errors can be avoided.

Besides, according to the system and the method for automatically calculating the specific uptake ratio of the striatum provided by the invention, after obtaining the range of each volume of interest in the nuclear medicine brain image, the specific uptake ratio of the striatum based on different background areas is calculated by calculating the average counts of each volume of interest.

Although the invention is described with reference to the above embodiments, the embodiments are not intended to limit the invention. A person of ordinary skill in the art may make variations and modifications without departing from the spirit and scope of the invention. Therefore, the protection scope of the invention should be subject to the appended claims.

What is claimed is:

1. A method for automatically calculating a specific uptake ratio of a striatum, comprising:
   obtaining a target image, wherein the target image comprises a nuclear medicine brain image;
   projecting the target image to a space coordinate to generate a projection amount;
   obtaining an upper end and a lower end of a brain in the target image based on a pixel gray value of the projection amount;
   setting a preset range from the upper end to the lower end as a striatum slice area in the target image;
   determining a brain area from the target image by using a line detection method;
   deforming a brain volume template according to the brain area and the striatum slice area, mapping a striatum in the brain volume template to the brain area in the target image, and delineating a striatum region in the target image;
   calculating counts of the striatum region as first average counts;
   setting another area of the target image as a background area, and calculating counts of the background area as second average counts; and
   calculating a specific uptake ratio of the target image according to the first average counts and the second average counts.

2. The method according to claim 1, wherein before projecting the target image to the space coordinate to generate the projection amount, the method further comprises:
   performing image spatial resolution conversion on the target image.

3. The method according to claim 1, wherein obtaining the upper end and the lower end of the brain in the target image based on the pixel gray value of the projection amount comprises:
   searching from an upper end point of the projection amount from top to bottom to a preset position, and taking a coordinate position of a pixel gray trough value from the upper end point to the preset position as the upper end; and
   searching from a lower end point of the projection amount from bottom to top to the preset position, and taking a coordinate position of a pixel gray trough value from the lower end point to the preset position as the lower end.

4. The method according to claim 3, wherein the preset position is ½ of an axial height of the projection amount.

5. The method according to claim 1, wherein the preset range is ½ to ⅔ of an axial height difference of the projection amount from the upper end to the lower end.

6. The method according to claim 1, wherein determining the brain area from the target image by using the line detection method comprises:
   extracting a plurality of target image slices of the target image in a range from the upper end to the lower end one by one;
   setting an image center of the target image slices as a picture center of a polar coordinate;
   transforming the target image slices from Cartesian coordinates to polar coordinates;
   detecting an image boundary to define a brain contour in the transformed target image slices; and
   transforming the target image slices having the brain contour back to the Cartesian coordinates, and determining the brain area from the target image.

7. The method according to claim 1, wherein deforming the brain volume template according to the brain area and the striatum slice area, mapping the striatum in the brain volume template to the brain area in the target image, and delineating the striatum region in the target image comprise:
   performing vertical axis scaling on the brain volume template according to the upper end, the lower end, and the striatum slice area;
   performing horizontal axis distortion on the scaled brain volume template by using a thin plate spline method;
   mapping the striatum in the adjusted brain volume template to the brain area in the target image; and
   delineating the striatum region in the target image and a center position of the striatum region.

8. The method according to claim 1, wherein calculating the counts of the striatum region as the first average counts comprises:
   calculating the first average counts of the striatum region according to total counts and total area of the striatum region.

9. The method according to claim 1, wherein the background area comprises an occipital lobe area, and calculating counts of the occipital lobe area as the second average counts comprises:
   setting a slice range downward from a position of the slice where the striatum slice area first appears from the upper end point of the projection amount from top to bottom;
   delineating the occipital lobe area in the slice range according to a divided area; and
   calculating the second average counts of the occipital lobe area according to total counts and total area of the occipital lobe area.

10. The method according to claim 1, wherein the background area comprises a cerebellum area, and calculating counts of the cerebellum area as the second average counts comprises:
    setting a slice range downward according to a position of the lower end of the brain;
    delineating the cerebellum area in the slice range according to a divided area; and
    calculating the second average counts of the cerebellum area according to total counts and total area of the cerebellum area.

11. The method according to claim 1, wherein the background area comprises a whole brain area, and calculating counts of the whole brain area as the second average counts comprises:
    calculating the second average counts according to total counts and total area of a portion of the brain area minus the striatum region.

12. The method according to claim 1, wherein calculating the specific uptake ratio of the target image according to the first average counts and the second average counts comprises:
   subtracting the second average counts from the first average counts and dividing the difference by the second average counts to obtain the specific uptake ratio.

13. A method for automatically delineating a striatum in a nuclear medicine brain image, comprising:
   obtaining a target image, wherein the target image comprises a nuclear medicine brain image;
   projecting the target image to a space coordinate to generate a projection amount;
   obtaining an upper end and a lower end of a brain in the target image based on a pixel gray value of the projection amount;
   setting a preset range from the upper end to the lower end as a striatum slice area in the target image;
   determining a brain area from the target image by using a line detection method;
   deforming a brain volume template according to the brain area and the striatum slice area, and mapping a striatum in the brain volume template to the brain area in the target image; and
   delineating a striatum region in the target image.

14. The method according to claim 13, wherein obtaining the upper end and the lower end of the brain in the target image based on the pixel gray value of the projection amount comprises:
   searching from an upper end point of the projection amount from top to bottom to a preset position, and taking a coordinate position of a pixel gray trough value from the upper end point to the preset position as the upper end; and
   searching from a lower end point of the projection amount from bottom to top to the preset position, and taking a coordinate position of a pixel gray trough value from the lower end point to the preset position as the lower end.

15. The method according to claim 14, wherein the preset position is ½ of an axial height of the projection amount.

16. The method according to claim 13, wherein the preset range is ½ to ⅔ of an axial height difference of the projection amount from the upper end to the lower end.

17. A system for automatically calculating a specific uptake ratio of a striatum, comprising:
   an image receiver, configured to receive a target image, wherein the target image comprises a nuclear medicine brain image; and
   an electronic device, comprising a storage device and a processor, wherein the storage device stores one or more instructions, and the processor is configured to execute the instructions to:
   obtain the target image;
   project the target image to a space coordinate to generate a projection amount;
   obtain an upper end and a lower end of a brain in the target image based on a pixel gray value of the projection amount;
   set ½ to ⅔ of an axial height difference of the projection amount from the upper end to the lower end as a striatum slice area in the target image;
   determine a brain area from the target image by using a line detection method;
   deform a brain volume template according to the brain area and the striatum slice area, map a striatum in the brain volume template to the brain area in the target image, and delineate a striatum region in the target image;
   calculate counts of the striatum region as first average counts;
   set another area of the target image as a background area, and calculate counts of the background area as second average counts; and
   calculate a specific uptake ratio of the target image according to the first average counts and the second average counts.

* * * * *